United States Patent [19]

Geigert et al.

[11] 4,426,449

[45] Jan. 17, 1984

[54] METHOD FOR PRODUCING VICINAL DIHALOGENTED PRODUCTS

[75] Inventors: John Geigert, Clayton; Saul L. Neidleman, Oakland, both of Calif.

[73] Assignee: Cetus Corporation, Berkeley, Calif.

[21] Appl. No.: 330,157

[22] Filed: Dec. 14, 1981

[51] Int. Cl.$^3$ ............................................. C12P 7/02
[52] U.S. Cl. ............................... 435/155; 435/156; 435/166; 435/189; 435/911
[58] Field of Search ............... 435/156, 155, 166, 132, 435/123, 189, 190, 911

[56] References Cited

U.S. PATENT DOCUMENTS

| | | |
|---|---|---|
| 3,528,886 | 9/1970 | Neidleman et al. |
| 3,934,037 | 1/1976 | Lewis et al. |
| 4,113,746 | 9/1978 | Kawabe et al. |
| 4,125,723 | 11/1978 | Beck et al. |
| 4,247,641 | 1/1981 | Neidleman et al. |

OTHER PUBLICATIONS

Hager, "Iodination of Tryosine by Chloroperoxidase: Preparation of Chloroperoxidase (Caldoriomyas Fumags)", Methods of. Enzymology, vol. 42A, pp. 648–653 (1970).
Hallenberg et al., "Panification of Chloroperoxidase from Calderiomyces fumags", *Methods of Enzymology*, vol. 52C, pp. 520–529 (1978).
Morrison et al., "Organic Chemistry", Allyn & Bacon Publisher, (1966), pp. 176–177, 182–185, 194–197, 242–245 and 898–899.
Cooney et al., *Biotechnology and Bioengineering*, vol. XVI, 1045–1053 (1974), Enzyme Catalysis in the Presence of Nonaqueous Solvents Using Chloroperoxidase.
Kollonitsch et al., *Haloperoxidase*, (1970), JACS 92: 4489, *J. Amer. Chem. So.*
Weissermel et al., *Industrial Organic Chemistry*, 191–200 (1978), Vinyl–Halogen and Vinyl–Oxygen Compounds.
Lowenhein et al., *Industrial Chemicals*, 389–391, (1975), Ethylene Dibromide.
Morris et al., *Biological Chemistry*, 1763–1768, (1966), Chloroperoxidase Isolation and Properties of the Crystalline Glycoprotein.

Primary Examiner—R. B. Penland
Attorney, Agent, or Firm—Fitch, Even, Tabin & Flannery

[57] ABSTRACT

A method is described for the manufacture of vicinal dihalogenated products from alkenes and alkynes by enzymatic reaction. The respective alkene or alkyne is contacted with a reaction mixture consisting of halogenating enzyme, an oxidizing agent and a halide ion source.

38 Claims, No Drawings

METHOD FOR PRODUCING VICINAL DIHALOGENATED PRODUCTS

This invention relates generally to an enzymatic process for making useful commercial products from alkenes and alkynes. More particularly, the invention relates to an improved process for the production of vicinal dihalogenated products from alkenes and alkynes wherein an enzyme is used to effect the reaction.

The manufacture of vicinal dihalogenated products from alkenes and alkynes forms an important part of industrial chemistry today. The products are useful as solvents, chemical intermediates, pesticides, monomers, and in many other ways. Ethylene dichloride (II), produced by the chlorination of ethylene (I), is consumed almost exclusively in the manufacture of vinyl chloride(III) (Weissermel et. al., *Industrial Organic Chemistry*, 191–200 (1978)).

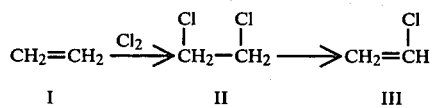

Ethylene dibromide (IV), produced by the bromination of ethylene (I), is used as a lead scavenger in gasoline and as a soil fumigant (Lowenheim et. al., *Industrial Chemicals*, 389–391 (1975)).

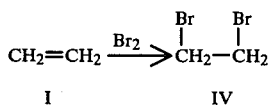

2,3-Dibromo-1-propanol (VI), produced by the bromination of allyl alcohol (V), is a valuable intermediate for incorporating a flame retarding dibromopropyl group into plastics and fibers (U.S. Pat. No. 4,125,723, Sandler, 1978), and is an active ingredient in increasing the feed efficiency of ruminant animals (U.S. Pat. No. 3,934,037, Lewis et. al., 1976).

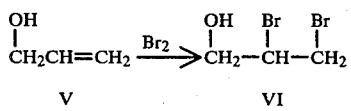

2,3-Dichloro-1-propanol (VII), produced by the chlorination of allyl alcohol (V) is a valuable intermediate for the manufacture of epichlorohydrin (VIII) which is a commercial material having particular utility as a starting material in the manufacture of epoxy resins (U.S. Pat. No. 4,113,746, Kawabe et al, 1978).

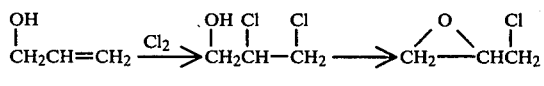

Known processes for producing the vicinal dihalogenated products from alkenes and alkynes typically involve the addition of alkene or alkyne and free halogen in a reactor under controlled conditions. The use of free halogen in these processes requires expensive control procedures and equipment to prevent loss of this toxic reactant. The use of free halogen is also preferably avoided because of the energy-intensive requirements for its production.

We have now developed an improved process for producing vicinal dihalogenated products from alkenes and alkynes. The enzymatic halogenating process of the present invention has several advantages over the present state of the art for producing vicinal dihalogenated products from alkenes and alkynes, including the following: The use of inexpensive, less dangerous, inorganic halide, rather then elemental halogen, i.e., chloride ion rather than chlorine; use of ambient temperature; and use of standard or nearly standard atmospheric pressure.

In addition to proceeding at room temperature, this enzymatic process involves the use of dilute $H_2O_2$, not necessarily purified. The $H_2O_2$ may be added directly or generated *in situ* by an enzymatic or chemical reaction. This reduces the cost of the $H_2O_2$ as compared to the cost of concentrated, purified material; increases the safe usage of the substance; and extends the life of the halogenating enzyme.

Accordingly, it is an object of the present invention to provide a process for preparing vicinal dihalogenated products from alkenes and alkynes.

It is also an object of the present invention to prepare these compounds without using free halogen.

It is a further object of the present invention to provide a low cost process for producing the desired products from alkenes and alkynes.

Other objects will become apparent to those skilled in the art from the following description.

Very generally, the method of the invention produces vinical dihalogenated products from alkenes and alkynes by providing in a reaction vessel a mixture of halogenating enzyme, an oxidizing agent and a halide ion source. An alkene or alkyne is then introduced into the vessel and maintained in contact with the reaction mixture for a sufficient period of time to convert the alkene or alkyne to the desired vicinal dihalogenated product.

The present invention is based on the discovery that the group of enzymes classified as haloperoxidases acts upon alkenes and alkynes to produce vicinal dihalogenated products. These products are characterized by the structural formula:

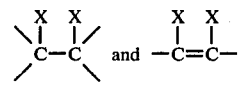

where X is selected from a group consisting of either chloride, bromide or iodide.

In the past, haloperoxidases have been used to produce halohydrins from alkenes; (U.S. Pat. No. 4,247,641 Neidleman et al, 1981) and haloketones and aldehydes from alkynes (U.S. patent application Ser. No. 229,554, Neidleman et al, filed Jan. 29, 1981).

Alkene

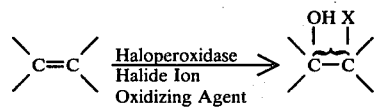

Alkyne

-continued

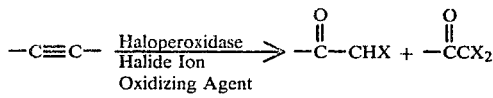

However, vicinal dihalogenated products have not heretofore been produced from alkenes and alkynes by haloperoxidases:

Alkene

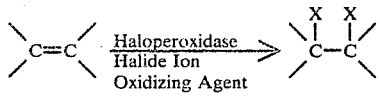

Alkyne

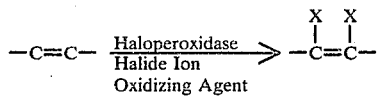

Moreover, it has not heretofore been obvious to run the alkene and alkyne reactions in the presence of very high levels of halide ion. U.S. Pat. No. 4,247,641 issued on Jan. 27, 1981 to Neidleman, et al and U.S. Pat. application Ser. No. 229,554 filed Jan. 29, 1981 by Neidleman, et al disclosed haloperoxidase reactions in halide concentrations ranging from 21 mM to 85 mM. U.S. Pat. No. 3,528,886 issued Sept. 15, 1970 to Neidleman, et al. disclosed haloperoxidase reactions in halide concentrations of 4 mM. Kollonitsch et al (J. Amer. Chem. Soc. 92, 4489-4490 (1972)) disclosed haloperoxidase reactions in halide concentration of 47 mM. Therefore, it was not obvious that haloperoxidase would produce totally different useful products from alkenes and alkynes when run in the presence of very high levels of halide ion (greater than 400 mM).

In accordance with this invention, a process has been developed for the production of vicinal dihalogenated products.

The term "alkene" as used in connection with the present invention is broadly defined as including any hydrocarbon containing a carbon-to-carbon double bond, represented by the following structural formula:

$$\underset{R^2}{\overset{R^1}{\diagdown}}C=C\underset{R^4}{\overset{R^3}{\diagup}}$$

wherein each of $R^1$, $R^2$, $R^3$ and $R^4$ is selected from a group consisting of:

(1) hydrogen
(2) a straight chain  ⎫ saturated or
(3) a branched chain ⎬ unsaturated
(4) a cyclic         ⎭ hydrocarbon radical Representative alkenes are:

| Alkene | $R^1$ | $R^2$ | $R^3$ | $R^4$ |
|---|---|---|---|---|
| ethylene | H | H | H | H |
| propylene | $CH_3$ | H | H | H |
| butene-1 | $C_2H_5$ | H | H | H |
| pentene-1 | $C_3H_7$ | H | H | H |
| octene-1 | $C_6H_{13}$ | H | H | H |
| decene-1 | $C_8H_{17}$ | H | H | H |
| dodecene-1 | $C_{10}H_{21}$ | H | H | H |

-continued (1) hydrogen
(2) a straight chain  ⎫ saturated or
(3) a branched chain ⎬ unsaturated
(4) a cyclic         ⎭ hydrocarbon radical Representative alkenes are:

| Alkene | $R^1$ | $R^2$ | $R^3$ | $R^4$ |
|---|---|---|---|---|
| isobutylene | $CH_3$ | $CH_3$ | H | H |
| cis-butene-2 | $CH_3$ | H | $CH_3$ | H |
| trans-butene-2 | $CH_3$ | H | H | $CH_3$ |
| 2-methyl-butene-2 | $CH_3$ | $CH_3$ | $CH_3$ | H |
| 1,3-butadiene | $CH_2=CH$ | H | H | H |
| 1,4-pentadiene | $H_2C=CHCH_2$ | H | H | H |
| isoprene | $H_2C=C(CH_3)$ | H | H | H |
| 1,7-octadiene | $H_2C=CH(CH_2)_4$ | H | H | H |

The term "alkene" in connection with the present invention broadly includes alkenes where $R^1$, $R^2$, $R^3$ and/or $R^4$ can be aromatic or heteroatom-containing group, provided that the substituents are inert to the prescribed reaction conditions and do not deactivate the normally reactive carbon-to-carbon double bond.

Representative alkenes containing such aromatic or heteroatom groups are:

| Alkene | $R^1$ | $R^2$ | $R^3$ | $R^4$ |
|---|---|---|---|---|
| methyl acrylate | $CH_3O_2C$ | H | H | H |
| allyl chloride | $ClCH_2$ | H | H | H |
| allyl bromide | $BrCH_2$ | H | H | H |
| allyl alcohol | $HOCH_2$ | H | H | H |
| 2-butene-1,4-diol | $HOCH_2$ | H | $HOCH_2$ | H |
| 2-buten-1-ol | $HOCH_2$ | H | H | $CH_3$ |
| 3-buten-1-ol | $HO(CH_2)_2$ | H | H | H |
| 4-penten-1-ol | $HO(CH_2)_3$ | H | H | H |
| styrene | $C_6H_5$ | H | H | H |

The R groups can be connected to form a cyclic ring. A representative cyclic alkene is 2-cyclohexen-1-ol (IX).

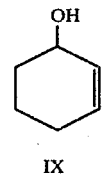

IX

The alkynes useful in the process of the invention can be broadly defined as any hydrocarbon containing a carbon-to-carbon triple bond, represented by the following structural formula:

$$R^1-C\equiv C-R^2$$

wherein each of $R^1$ and $R^2$ is selected from a group consisting of:

(1) hydrogen
(2) a straight chain  ⎫ saturated or
(3) a branched chain ⎬ unsaturated
(4) a cyclic         ⎭ hydrocarbon radical Representative alkynes are:

| Alkyne | $R^1$ | $R^2$ |
|---|---|---|
| acetylene | H | H |
| methyl acetylene | $CH_3$ | H |
| ethyl acetylene | $CH_3CH_2$ | H |
| 1-phenyl-1-propyne | $C_6H_5$ | $CH_3$ |
| propargyl alcohol | $HOCH_2$ | H |

| -continued | | |
|---|---|---|
| (1) hydrogen<br>(2) a straight chain<br>(3) a branched chain<br>(4) a cyclic | } | saturated or<br>unsaturated<br>hydrocarbon radical |
| Representative alkynes are: | | |
| Alkyne | $R^1$ | $R^2$ |
| 2-butyne-1,4-diol | $HOCH_2$ | $HOCH_2$ |
| 3-butyn-1-ol | $HO(CH_2)_2$ | H |

The present invention makes use of haloperoxidase enzymes. Such enzymes include chloroperoxidase derived from the microorganism *Caldariomyces fumago*, bromoperoxidase derived from algae, lactoperoxidase derived from milk, thyroid peroxidase derived from the thyroid, myeloperoxidase derived from leukocytes, and horseradish peroxidase derived from horseradish. Certain of these haloperoxidases are commercially available.

The preferred haloperoxidase depends upon the products desired. The halides that the given haloperoxidase can use are listed below:

| Haloperoxidase | Halides |
|---|---|
| myeloperoxidase | $Cl^-, Br^-, I^-$ |
| chloroperoxidase | $Cl^-, Br^-, I^-$ |
| lactoperoxidase | $Br^-, I^-$ |
| bromoperoxidase | $Br^-, I^-$ |
| thyroid peroxidase | $I^-$ |
| horseradish peroxidase | $I^-$ |

For ease of discussion, various aspects of the present invention are described with particularity, but not exclusively, in connection with the use of the preferred peroxidase, chloroperoxidase, derived from *Caldariomyces fumago*. The microorganism, *Caldariomyces fumago*, may be grown as a static or agitated, submerged culture in Czapek-Dox medium at room temperature for 3 to 10 days by conventional methods. The halogenating enzyme, chloroperoxidase, is prepared from an aqueous homogenate of the mycelial pads of the microorganism grown under static conditions or from the filtrate of the microorganism grown under static or agitated submerged culture conditions. Detailed descriptions for preparing chloroperoxidase can be found in the following articles and patent:

(1) U.S. Pat. No. 4,247,641 issued to Neidleman et al., on Jan. 27, 1981; (2) Morris et al., *J. Biol. Chem.* 241, 1763–1768 (1966); and (3) Cooney et al., *Biotech. Bioeng.* 16, 1045–1053 (1974).

The halogenating enzyme may also be used in an immobilized form. Processes for enzyme immobilization are familiar to those skilled in the art, and include reacting either a solution of the enzyme or a suspension of enzyme containing cells with one of a broad range of organic or inorganic supports. Included among these are polyacrylamide, ethylene-maleic acid copolymers, methacrylic-based polymers, polypeptides, styrene-based polymers, agarose, cellulose, dextran, porous glass beads, and aluminum or titanium hydroxide. Enzymes in this form have increased stability, extended life and usefulness, and recoverability. Reactions employing immobilized enzymes may be run in columns or reaction tanks.

In addition to the halogenating enzymes, an oxidizing agent is required in the reaction mixture. A preferred oxidizing agent, hydrogen peroxide, is added directly to the mixture in a single batch addition, or in a continuous slow feed. It is alternatively generated as a slow feed in situ by the use of a hydrogen peroxide-producing enzyme system. Such enzyme systems are well known in the art, and include glucose-1-oxidase in the presence of D-glucose, pyranose-2-oxidase or glucose-2-oxidase in the presence of D-glucose, D- and L-amino acid oxidases in the presence of D- and L-methionine, methanol oxidase in the presence of methanol, and diamine oxidases in the presence of histamine. The hydrogen peroxide-generating system is present in the non-immobilized or immobilized state as with the halogenating enzyme. The hydrogen peroxide is also generated by a chemical reaction, such as the anthraquinone or isopropyl alcohol oxidation processes.

The hydrogen peroxide is present preferably in molar ratio of from about 0.5:1 to about 50:1, most preferably in a ratio of about 1:1 or less with respect to the alkene or alkyne. The molar ratio preferences refer to the average presence of hydrogen peroxide during the reaction. The actual molar ratio usually varies during the reaction and at any particular time may be above or below the ranges cited. Other suitable oxidizing agents include organic peroxides, such as methyl, ethyl, or butyl peroxides.

A source of inorganic halide is also required in the reaction mixture. The halide ion source may be any of the water-soluble halide salts. The preferred halide ion sources are the chloride, bromide, and iodide salts of the alkali metals, sodium, potassium and lithium. The halide ion is present at a level greater than 400 mM.

The reaction is conducted with the pH range of from about 2.2 to about 8.0. The pH of the reaction is preferably maintained within the desired range by use of a buffering agent. Suitable buffers include sodium or potassium phosphate, gluconate, citrate, formate, and acetate based systems. Other suitable techniques besides buffering may also be used for pH control and adjustment.

The reaction is conducted in an aqueous medium. While some of the alkenes and alkynes that can be converted by the process are substantially insoluble in an aqueous medium, the reaction, nevertheless, occurs satisfactorily under conditions of mixing, or other modes of dispersion, which provide sufficient substrate solubility for the reaction.

The reaction may also be conducted, if desired or necessary, in the presence of aqueous organic solvent mixtures, such as water solutions containing lower aliphatic alcohols, dioxane, dimethylformamide, dimethylsulfoxide or glycerol, in order to increase substrate solubility.

The reaction is preferably conducted under aerobic conditions and in the temperature range of 15° C. to about 50° C., preferably at 20° to about 30°.

As previously indicated, the components of the reaction mixture, namely the alkene or alkyne, the halogenating enzyme, the oxidizing agent, the halide ion source, and the buffering agent, are simply mixed together in water or mixed aqueous or organic media, and agitated for a period of, for example, from about 30 seconds to about 1 hour to obtain the dihalogenated products.

The reaction for alkenes is represented by the following equation:

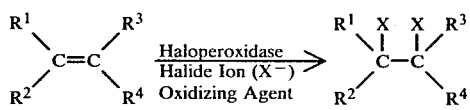

The reaction for alkynes is represented by the following equation:

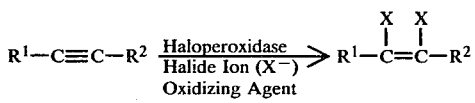

The products obtained by such reactions according to the present invention were quantitated by gas chromatography (GC) using flame ionization detection (FID). Five (5) µl of the reaction mixture were injected into a Varian 3700 GC, equipped with a 6 foot×4 mm coiled, glass column packed with Tenax-GC (80/100 mesh). The flow rate through the column was set at 40 ml/minute of helium. The column temperature was operated isothermally (specific temperature given in each example); the injection temperature was set at 240° C.; and the detector temperature was set at 240° C.

The products were identified by gas chromatography-mass spectrometry (GCMS). Ten (10) µl of the reaction mixture was injected into a Finnigan 4021 GCMS, equipped with a 6 foot×4 mm coiled, glass column packed with Tenax-GC (80/100 mesh). Flow rate through the column was set at 30 ml/minute of helium. The column temperature was operated isothermally (specific temperature given in each example); the injection temperature was set at 240° C.; and the jet separator was set at 240° C. The mass spectrometer was operated at 70 eV, electron impact ionization.

The following examples are intended only to further illustrate the invention and are not intended to limit the scope of the invention which is defined by the claims.

EXAMPLE 1

Potassium chloride (1.7 g; 2290 mM final), potassium phosphate buffer at pH 3.5 (10 ml, 0.1 M), hydrogen peroxide (4.1 mg; 137 µl of a 3% solution; 12 mM final) and allyl alcohol (7.0 mg; 12 mM final; $HOCH_2CH=CH_2$; purchased from Aldrich Chemical Company, Milwaukee, WI) were mixed together in a 25 ml Pyrex flask at room temperature and room pressure. The haloperoxidase enzyme, chloroperoxidase (0.4 ml) was then added. The reaction was concluded 15 minutes after the addition of the last reagent.

The chloroperoxidase was prepared as follows:

Mycelial pads of *Caldariomyces fumago* (ATCC 16373) were grown on potato agar slants. Sliced potato (200 g) was cooked in distilled water (500 ml) for 40 minutes and then strained. A solution of glucose (21 g) and agar (20 g) in distilled water (500 ml) was added to the strained solution. The pH was adjusted to 6.8 and the volume was brought to 1 liter with distilled water. The medium was sterilized at 121° C. for 15 minutes.

The organism was inoculated on the potato agar slants, produced in accordance with the above procedure, and was grown for about one week at room temperature. The organism was then used to inoculate a soybean-glucose medium (50 ml). The soybean-glucose medium was prepared by adding, to 1 liter of distilled water, extraction process soybean meal (30 g), glucose (30 g), and $CaCO_3$ (7 g). The medium was sterilized at 121° C. for 30 minutes and was then inoculated with the organism after cooling.

The organism was grown for 4–5 days on a rotary shaker at 25°. Five ml of this material was used to inoculate a 500 ml Erlenmeyer flask containing 100 ml of a modified Czapek-Dox medium prepared by adding the following to 1 liter of distilled water: $NaNO_3$ (3 g), $KH_2PO_4$ (1 g), KCl (0.5 g), $MgSO_4.7H_2O$ (0.5 g), $FeSO_4.7H_2O$ (10 mg), and glucose (40 g). The medium was sterilized at 121° for 20 minutes prior to inoculation with the organism.

The organism was grown under static conditions at room temperature for 5–7 days. The black mycelial pads which formed were collected, rinsed with distilled water, and stored in plastic bags in a freezer at $-10°$ C. for subsequent use.

The halogenating enzyme was prepared by grinding 6 mycelial pads (prepared in accordance with the above procedures) with 60 g acid-washed sand and 60 ml distilled water for 2 minutes in a Virtis 45 homogenizer. The homogenate was centrifuged while cold and the supernatant solution was used as the source of the halogenating enzyme, chloroperoxidase.

The final chloroperoxidase supernatant was filtered through Whatman No. 1 paper at room temperature. The filtrate was concentrated about 10-fold using a rotary film evaporator at reduced pressure and temperature ($<35°$ C.). The concentrate was chilled at 0° in an ice bath, and pre-chilled (0° C.) ethanol was added until 45% ethanol (v/v) was reached. The mixture was stirred vigorously for 15 minutes, and then centrifuged at $-10°$ C. (at 15,000 g) with a 55-34 rotor in a Sorval RC-5 Superspeed for 15 minutes. The black sediment was discarded. To the centrifugate, cooled at 0° C., was added additional prechilled ethanol to give 65% ethanol (v/v). The mixture was slowly stirred for 30 minutes at 0° C., and then centrifuged as before. The centrifugate was was discarded, and the precipitate containing the chloroperoxidase activity was dissolved in 1 ml of 0.05 M potassium phosphate (pH 7). The enzyme solution was stored at $-20°$ C.

The products were quantitated by gas chromatography (GC) using flame ionization detection (FID). Five (5) µl of the reaction mixture was injected into a Varian 3700 GC, equipped with a 6 foot×4 mm coiled, glass column packed with Tenax-GC (80/mesh). Flow rate through the column was set at 40 ml/minute of helium. The column temperature was 190° C., isothermal; the injection temperature was set at 240° C.; and the detector temperature was set at 240° C.

The products were identified by gas chromatography-mass spectrometry (GCMS). 10 µl of the reaction mixture was injected into a Finnigan 4021 GCMS, equipped with a 6 foot×4 mm coiled, glass column packed with Tenax-GC (80/100 mesh). Flow rate through the column was set at 30 ml/minute of helium. The column temperature was 190° C., isothermal; the injection temperature was set at 240° C.; and the jet separator was set at 240° C. The mass spectrometer was operated at 70 eV, electron impact ionization.

Four products were detected.

The major product had a GC retention time of 6 minutes and showed the mass spectrum diagnostic for 2,3-dichloro-1-propanol: molecular mass ion not detected; major fragment mass ions at mass 92 and 94 (3:1 in intensity; loss of HCl from molecular ion), and at mass 62 and 64 (3:1 in intensity; the $CH_2=CH-Cl^+$ ion). This product had an identical GC retention time and mass spectrum with that of an authentic sample of 2,3-dichloro-1-propanol (purchased from Aldrich Chemical Company).

Two minor products had GC retention times of 7 and 8 minutes, and showed the mass spectra diagnostic for chloropropanediols. The product having a 7 minute retention time was identified as 1-chloro-2,3-propanediol: molecular mass ion not detected; major fragment mass ions at mass 79 and 81 (3:1 in intensity; loss of $CH_2OH$ from the molecular ion), and at mass 61 (loss of $CH_2Cl$ from molecular ion). The product having an 8 minute retention time was identified as 2-chloro-1,3-propanediol: molecular mass ion not detected; major fragment mass ions at mass 92 and 94 (3:1 in intensity; loss of $H_2O$ from molecular ion), and at mass 62 and 64 (3:1 in intensity; the $CH_2\!=\!CH\!-\!Cl^+$ ion).

A third minor product had a GC retention time of 1 minute and showed the mass spectrum diagnostic for acrolein: molecular mass ion at mass 56; major fragment mass ion at mass 55 (loss of H from molecular ion).

The following summarizes the products obtained:

| Product | % of Total Yield |
|---|---|
| OH Cl Cl<br>\|   \|   \|<br>$CH_2$—CH—$CH_2$ | 91 |
| OH OH Cl<br>\|   \|   \|<br>$CH_2$—CH—$CH_2$ | 5 |
| OH Cl OH<br>\|   \|   \|<br>$CH_2$—CH—$CH_2$ | 3 |
| O<br>\|\|<br>CH—CH=$CH_2$ | 1 |
| Total Yield = | 5.4 mg |

Further, the major product, 2,3-dichloro-1-propanol was converted to epichlorohydrin by addition of lime to the aqueous reaction mixture until the pH was greater than 10. Identity of epichlorohydrin was confirmed by gas chromatography/mass spectrometry comparison with an authentic sample (purchased from Aldrich Chemical Company).

Also, the major product 2,3-dichloro-1-propanol was converted to epichlorohydrin by addition of Flavobacterium sp. whole cells to the aqueous reaction mixture, as set forth in U.S. Pat. No. 4,247,641 issued to Neidleman et al on Jan. 27, 1981.

EXAMPLE 2

This example demonstrates the control of the ratio of dihalo-product to halohydrin by controlling the level of halide salt in the reaction.

The procedure for Example 1 was followed, except: (1) potassium bromide was substituted for potassium chloride, (2) lactoperoxidase (purchased from Sigma Chemical Company, St. Louis, MO, Catalog No. L-7129; 0.5 ml used per reaction) was substituted for chloroperoxidase, and (3) the buffer pH was set at 6.5 rather than 3.5. The final concentration of potassium bromide in the reactions were 17 mM, 423 mM and 3389 mM, respectively.

Analysis of products by GC and GCMS was as outlined in Example 1.

One product had a GC retention time of 16 minutes and showed the mass spectrum diagnostic for 2,3-dibromo-1-propanol: molecular mass ion at mass 216, 218 and 220 (1:2:1 in intensity) indicating 2 bromine atoms on the molecule; major fragment mass ions at 137 and 139, and at 136 and 138 (both sets 1:1 in intensity; loss of Br and HBr, respectively, from molecular ion), and at mass 106 and 108 (1:1 in intensity; the $CH_2\!=\!CH\!-\!BR^+$ ion). This product had an identical GC retention time and mass spectrum with that of an authentic sample of 2,3-dibromo-1-propanol (purchased from Aldrich Chemical Company).

Two other products had GC retention times of 10 and 12 minutes, and showed the mass spectra diagnostic for bromopropanediols. The product having a 10 minute retention time was identified as 1-bromo-2,3-propanediol: molecular ion not detected; major fragment mass ions at mass 123 and 125 (1:1 in intensity; loss of $CH_2OH$ from molecular ion), and at mass 61 (loss of $CH_2Br$ from molecular ion). The product having a 12 minute retention time was identified as 2-bromo-1,3-propanediol: molecular mass ion not detected; major fragment mass ions at mass 136 and 138 (1:1 in intensity; loss of $H_2O$ from molecular ion), and at mass 106 and 108 (1:1 in intensity; the $CH_2\!=\!CH\!-\!Br^+$ ion).

The following summarizes the products obtained as a function of halide concentration in the reaction mixture:

| | % of Total Yield | | | |
|---|---|---|---|---|
| Product | 17 | 423 | 3389 | mM KBr |
| OH Br Br<br>\|   \|   \|<br>$CH_2$—CH—$CH_2$ | 18 | 65 | 98 | |
| OH OH Br<br>\|   \|   \|<br>$CH_2$—CH—$CH_2$ | 43 | 19 | 1 | |
| OH Br OH<br>\|   \|   \|<br>$CH_2$—CH—$CH_2$ | 39 | 16 | 1 | |
| Total Yield | 5.1 mg | 11.9 mg | 20.8 mg | |

Further, the product 2,3-dibromo-1-propanol was converted to epibromohydrin by addition of either lime or Flavobacterium sp. whole cells, as outlined in Example 1. Identity of epobromohydrin was confirmed by gas chromatography/mass spectrometry comparison with an authentic sample (purchased from Aldrich Chemical Company).

EXAMPLE 3

The procedure of Example 2 was followed except (1) potassium bromide was added to only one level (3389 mM final) and (2) in situ generation of hydrogen peroxide was made by adding β-D-glucose (25 mg) and glucose-1-oxidase (0.05 ml; purchased from Sigma Chemical Company, Catalog No. G-6500). The reaction was allowed to proceed for 2 hours.

The following summarizes the products obtained:

| Product | % of Total Yield |
|---|---|
| OH Br Br<br>\|   \|   \|<br>$CH_2$—CH—$CH_2$ | 97 |

-continued

| Product | % of Total Yield |
|---|---|
| OH OH Br<br> \|    \|    \|<br>$CH_2-CH-CH_2$ | 2 |
| OH Br OH<br> \|    \|    \|<br>$CH_2-CH-CH_2$ | 1 |
| Total Yield = | 12.2 mg |

EXAMPLE 4

The procedure of Example 3 was followed except: (1) sodium iodide was added to only one level (1.2 g; 800 mM final) and (2) horseradish peroxidase (2 mg; purchased from Sigma Chemical Company, Catalog No. P-8375) was used instead of lactoperoxidase.

Three products were detected. The GC column temperature was set at 220° C., isothermal.

One product had a GC retention time of 23 minutes and showed the mass spectrum diagnostic for 2,3-diiodo-1-propanol: molecular mass ion not detected; major fragment mass ions at mass 254 (the $I_2^+$ ion), at mass 185 (loss of I from molecular ion), at mass 127 (the $I^+$ ion), and at mass 57 (loss of $HI_2$ from molecular ion.

Two other products had GC retention times of 4 and 6 minutes, and showed the mass spectra diagnostic for iodopropanediols. The product having a 4 minute retention time was identified as 1-iodo-2,3-propanediol: molecular mass ion at mass 202; major fragment mass ions at mass 171 (loss of $CH_2OH$ from molecular ion) and at mass 75 (loss of I from molecular ion). The product having a 6 minute retention time was identified as 2-iodo-1,3,-propanediol: molecular mass ion at mass 202; major fragment mass ions at mass 154 (loss of $CH_2OH+OH$ from molecular ion), at mass 127 (the $I^+$ ion) and at mass 75 (loss of I from molecular ion).

Molecular iodine ($I_2$) was also formed.

The following summarizes the products obtained:

| Product | % of Total Yield |
|---|---|
| OH I I<br> \|    \|    \|<br>$CH_2-CH-CH_2$ | 72 |
| OH OH I<br> \|    \|    \|<br>$CH_2-CH-CH_2$ | 18 |
| OH I OH<br> \|    \|    \|<br>$CH_2-CH-CH_2$ | 10 |
| Total Yield = | 8.1 mg |

EXAMPLE 5

The procedure of Example 1 was followed, except: (1) potassium bromide (4 g; 3389 mM final) was substituted for potassium chloride. The following hydroxy-containing alkenes were run: 3-buten-1-ol; 3-buten-2-ol; and 4-penten-1-ol (8.6, 8.6 and 10.3 mg, respectively; 12 mM final; all purchased from Aldrich Chemical Company).

With 3-buten-1-ol ($HOCH_2CH_2CH=CH_2$), three products were detected. The GC column temperature was set at 200° C., isothermal.

The major product had a GC retention time of 15 minutes and showed the mass spectrum diagnostic for 1,2-dibromo-4-butanol: molecular mass ion not detected; major fragment mass ions at mass 185, 187 and 189 (1:2:1 in intensity; loss of $CH_2CH_2OH$ from molecular ion), at mass 151 and 153 (1:1 in intensity; loss of Br from molecular ion) and at mass 133 and 135 (1:1 in intensity; loss of $H_2O+Br$ from the molecular ion).

Two minor products had GC retention times of 9 and 10 minutes, and showed the mass spectra diagnostic for bromobutanediols. The product haveing a 9 minute retention time was identified as 1-bromo-2,4-butanediol: molecular ion not detected; major fragment mass ions at mass 150 and 152 (1:1 in intensity; loss of $H_2O$ from molecular ion) and at mass 123 and 125 (1:1 in intensity; loss of $CH_2CH_2OH$ from molecular ion). The product having a 10 minute retention time was identified as 2-bromo-1,4-butanediol.

With 3-buten-2-ol ($CH_3CH(OH)CH=CH_2$), three products were detected. The GC column temperature was set at 200° C. isothermal.

The major product had a GC retention time of 14 minutes and showed the mass spectrum diagnostic for 1,2-dibromo-3-butanol: molecular ion not detected; major fragment mass ions at mass 215, 217 and 219 (1:2:1 in intensity; loss of $CH_3$ from the molecular ion), at mass 185, 187 and 189 (1:2:1 in intensity; loss of $CH_3CH-OH$ from the molecular ion), and at mass 45 (the $CH_3CH=OH^+$ ion).

Two minor products had GC retention times of 8 and 9 minutes, and showed the mass spectra diagnostic for bromobutanediols. The product having an 8 minute retention time was identified as 1-bromo-2,3-butanediol: molecular ion not detected; major fragment mass ions at mass 153 and 155 (1:1 in intensity; loss of $CH_3$ from molecular ion), at mass 123 and 125 (1:1 in intensity; loss of $CH_3CH-OH$ from the molecular ion) and at mass 45 (the $CH_3CH=OH^+$ ion). The product having a 9 minute retention time was identified as 2-bromo-1,3-butanediol.

With 4-penten-1-ol ($HOCH_2CH_2CH_2CH=CH_2$), three products were detected. The GC column temperature was set at 200° C., isothermal.

One major product had a GC retention time of 18 minutes and showed the mass spectrum diagnostic for 1,2-dibromo-5-pentanol: molecular mass ion not detected; major fragment mass ions at mass 165 and 167 (1:1 in intensity; loss of HBr from the molecular ion), and at mass 147 and 149 (1:1 in intensity; loss of $H_2O+Br$ from the molecular ion).

Two other products had GC retention times of 12 and 13 minutes, and showed the mass spectra diagnostic for bromopentanediols. The product having a 12 minute retention time was identified as 1-bromo-2,5-pentanediol: molecular ion not detected; major fragment mass ions at mass 164 and 166 (1:1 in intensity; loss of $H_2O$ from molecular ion), and at mass 123 and 125 (1:1 in intensity; loss of $CH_2CH_2CH_2OH$ from the molecular ion). The product having a 13 minute retention time was identified as 2-bromo-1,5-pentanediol.

The following summarizes the products obtained:

| | % of Total Product Yield | | |
|---|---|---|---|
| Substrate | OH<br>\|<br>R—CH—(CH$_2$)$_n$—CH—CH$_2$<br>\|    \|<br>Br   Br | OH              OH  Br<br>\|                    \|   \|<br>R—CH—(CH$_2$)$_n$—CH—CH$_2$ | Total Yield |
| 3-buten-1-ol<br>(R = H; n = 1) | 85 | 15 | 13.3 mg |
| 3-buten-2-ol<br>(R = CH$_3$; n = O) | 92 | 8 | 13.7 mg |
| 4-penten-1-ol<br>(R = H; n = 2) | 49 | 51 | 8.2 mg |

EXAMPLE 6

The procedure of Example 1 was followed, except 2-butene-1,4-diol (10.5 mg; 12 mM final; HOCH$_2$CH=CHCH$_2$OH; purchased from Aldrich Chemical Company) was substituted for allyl alcohol.

One product was detected. The GC column temperature was set at 210° C., isothermal.

The product had a GC retention time of 12 minutes and showed the mass spectrum diagnostic for 2,3-dichloro-1,4-butanediol: molecular mass ion not detected; major fragment mass ions at mass 123 and 125 (3:1 in intensity; loss of Cl from the molecular ion), and at mass 105 and 107 (3:1 in intensity; loss of Cl+H$_2$O from the molecular ion).

The following summarizes the products obtained:

| Product | % of Total Yield |
|---|---|
| OH  Cl  Cl  OH<br>\|     \|    \|    \|<br>CH$_2$—CH—CH—CH$_2$ | 100 |
| OH  OH  Cl  OH<br>\|     \|    \|    \|<br>CH$_2$—CH—CH—CH$_2$ | not detected |
| Total Yield - | 4.4 mg |

EXAMPLE 7

The procedure of Example 6 was followed except potassium bromide (4 g; 3389 mM final) was substituted for potassium chloride.

Three products were detected. The GC column temperature was set at 210° C., isothermal.

The major product had a GC retention time of 19 minutes and showed the mass spectrum diagnostic for 2,3-dibromo-1,4-butanediol: molecular mass ion not detected; major fragment mass ions at mass 198, 200 and 202 (1:2:1 in intensity; loss of CH$_2$OH+OH from molecular ion), at mass 167 and 169 (1:1 in intensity; loss of Br from molecular ion), and at mass 149 and 151 (1:1 in intensity; loss of Br+H$_2$O from molecular ion).

One minor product had a GC retention time of 13 minutes, and showed the mass spectrum diagnostic for 2-bromo-1,3,4-butanetriol: molecular mass ion not detected; major fragment mass ions at mass 153 and 155 (1:1 in intensity; loss of CH$_2$OH from molecular ion), and at mass 123 and 125 (1:1 in intensity; loss of CH(OH)CH$_2$OH from molecular ion).

The second minor product was identified as 4-hydroxy-2-buten-1-al (HOCH$_2$CH=CHCHO).

The following summarizes the products obtained:

| Product | % of Total Yield |
|---|---|
| OH  Br  Br  OH<br>\|     \|    \|    \|<br>CH$_2$—CH—CH—CH$_2$ | 93 |
| OH  OH  Br  OH<br>\|     \|    \|    \|<br>CH$_2$—CH—CH—CH$_2$ | 5 |
| OH<br>\|<br>CH$_2$—CH=CHCHO | 2 |
| Total Yield = | 14.2 mg |

EXAMPLE 8

This example further demonstrates the control of the ratio of dihalo-product to halohydrin by controlling the level of halide salts in the reaction.

Potassium bromide (60 mg and 4956 mg, respectively; 51 mM and 4200 mM final), potassium phosphate buffer at pH 3.5 (10 ml, 0.1 M), hydrogen peroxide (4.1 mg; 12 mM final) and allyl chloride (9.1 mg; 12 mM final: ClCH$_2$CH=CH$_2$; purchased from Aldrich Chemical Company) were mixed together in a 25 ml Pyrex flask at room temperature and room pressure. The haloperoxidase enzyme, chloroperoxidase (0.4 ml), was then added. The reaction was concluded 15 minutes after the addition of the last reagent.

Analysis of products by GC and GCMS was as outlined in Example 1. The GC column temperature was set at 190° C., isothermal. Three products were detected.

One product had a GC retention time of 15 minutes and showed the mass spectrum diagnostic for 1,2-dibromo-3-chloropropane: molecular mass ion not detected; major fragment mass ions at mass 185, 187 and 189 (1:2:1 in intensity; loss of CH$_2$Cl from molecular ion), at mass 155, 157 and 159 (3:4:1 in intensity; loss of Br from molecular ion), at mass 75 and 77 (3:1 in intensity; loss of HBr$_2$ from molecular ion), at mass 93 and 95 (1:1 in intensity; the CH$_2$=Br$^+$ ion), and at mass 49 and 51 (3:1 in intensity; the CH$_2$=Cl$^+$ ion).

Two products had GC retention times of 9 and 11 minutes, respectively, and showed the mass spectra diagnostic for bromochloropropanols. The product having an 11 minute retention time was identified as 2-bromo-1-chloro-3-propanol: molecular mass ion at mass 172, 174 and 176 (3:4:1 in intensity) indicating the presence of one bromine atom and one chlorine atom on the molecule; major fragment mass ions at mass 136 and 138 (1:1 in intensity; loss of HCl from molecular ion), at mass 106 and 108 (1:1 in intensity; the CH$_2$=CH—Br$^+$ ion), and at mass 49 and 51 (3:1 in intensity; the CH$_2$=Cl$^+$ ion).

The product having a 9 minute retention time was identified as 1-bromo-3-chloro-2-propanol: molecular mass ion at mass 172, 174 and 176 (3:4:1 in intensity) indicating the presence of one bromine atom and one chlorine atom on the molecule; major fragment mass ions at mass 123 and 125 (1:1 in intensity; loss of $CH_2Cl$ from molecular ion), and at mass 79 and 81 (3:1 in intensity; loss of $CH_2Br$ from molecular ion).

The following summarizes the products obtained as a function of halide concentration in the reaction mixture:

| Product | % of Total Yield | | mM KBr |
|---|---|---|---|
| | 51 | 4200 | |
| Cl Br Br<br>$\|$ $\|$ $\|$<br>$CH_2$—CH—$CH_2$ | 4 | 82 | |
| Cl OH Br<br>$\|$ $\|$ $\|$<br>$CH_2$—CH—$CH_2$ | 33 | 6 | |
| Cl Br OH<br>$\|$ $\|$ $\|$<br>$CH_2$—CH—$CH_2$ | 63 | 12 | |
| Total Yield | 8.5 mg | 13.3 mg | |

EXAMPLE 9

The procedure of Example 8 was followed, except allyl bromide (14.4 mg; 12 mM final; $BrCH_2CH=CH_2$; purchased from Aldrich Chemical Company) was substituted for allyl chloride.

Three products were detected. The GC column temperature was set at 190° C., isothermal.

One product had a GC retention time of 31 minutes and showed the mass spectrum diagnostic for 1,2,3-tribromopropane: molecular mass ion not detected; major fragment mass ions at mass 199, 201 and 203 (1:2:1 in intensity; loss of Br from molecular ion), at mass 119 and 121 (1:1 in intensity; loss of $HBr_2$ from molecular ion), and at mass 93 and 95 (1:1 in intensity; the $CH_2=Br^+$ ion). This product had an identical GC retention time and mass spectrum with that of an authentic sample of 1,2,3-tribromopropane (purchased from Aldrich Chemical Company).

Two products had GC retention times of 14 and 16 minutes, respectively, and showed the mass spectrum diagnostic for dibromopropanols. The product having a 16 minute retention time was identified as 2,3-dibromo-1-propanol: molecular mass ion not detected; major fragment mass ions at mass 137 and 139 (1:1 in intensity; loss of Br from molecular ion), at mass 136 and 138 (1:1 in intensity; loss of HBr from molecular ion), at mass 106 and 108 (1:1 in intensity; the $CH_2=CH—Br^+$ ion), and at mass 57 (loss of $HBr_2$ from molecular ion). The product having a 14 minute retention time was identified as 1,3-dibromo-2-propanol.

The following summarizes the products obtained as a function of halide concentration in the reaction mixture:

| Product | % of Total Yield | | mM KBr |
|---|---|---|---|
| | 51 | 4200 | |
| Br Br Br<br>$\|$ $\|$ $\|$<br>$CH_2$—CH—$CH_2$ | 2 | 77 | |
| Br OH Br<br>$\|$ $\|$ $\|$<br>$CH_2$—CH—$CH_2$ | 28 | 8 | |
| Br Br OH<br>$\|$ $\|$ $\|$<br>$CH_2$—CH—$CH_2$ | 70 | 15 | |
| Total Yield | 8.3 mg | 10.7 mg | |

EXAMPLE 10

The procedure of Example 1 was followed, except styrene (12 mg; 12 mM final; $C_6H_5$—CH=$CH_2$; purchased from Aldrich Chemical Company) was substituted for allyl alcohol.

Two products were detected. The GC column temperature was set at 210° C., isothermal.

One product had a GC retention time of 10 minutes, and showed the mass spectrum diagnostic for 1,2-dichloro-1-phenylethane: molecular mass ion at mass 174, 176 and 178 (10:6:1 in intensity) indicating two chlorine atoms on the molecule; major fragment mass ions at mass 139 and 141 (3:1 in intensity; loss of Cl from molecule ion), and at mass 125 and 127 (3:1 in intensity; loss of $CH_2Cl$ from molecular ion).

The other product had a GC retention time of 12 minutes, and showed the mass spectrum diagnostic for 2-chloro-1-phenylethanol: molecular mass ion at mass 156 and 158 (3:1 in intensity) indicating one chlorine atom on the molecule; major fragment mass ions at mass 120 (loss of HCl from molecular ion) and at mass 107 (loss of $CH_2Cl$ from molecular ion).

The following summarizes the products obtained:

| Product | % of Total Yield |
|---|---|
| $C_6H_5$—CH(Cl)—$CH_2$Cl | 24 |
| $C_6H_5$—CH(OH)—$CH_2$Cl | 76 |
| Total Yield | 8.2 mg |

EXAMPLE 11

This example further demonstrates the control of the ratio of dihalo-product to halohydrin by controlling the level of halide salt in the reaction.

Potassium bromide (47 mg and 4956 mg, respectively; 40 mM and 4200 mM final) and potassium phosphate buffer at pH 3.5 (10 ml, 0.1 M) were mixed together in a 50 ml Pyrex flask at room temperature and room pressure. Ethylene ($CH_2=CH_2$; purchased from Matheson Gas Products, Lyndhurst, N.J.), a gaseous alkene, was slowly (10 ml/min) and continuously bubbled through the reaction mixture. After 15 minutes, the haloperoxidase enzyme chloroperoxidase (0.4 ml), was then added. Finally hydrogen peroxide (4.1 mg; 12 mM final) was added. The reaction was concluded 15 minutes after the addition of the last reagent.

Analysis of products by GC and GCMS was as outlined in Example 1. The GC column temperature was set at 170° C., isothermal. Two products were detected.

One product had a GC retention time of 7 minutes and showed the mass spectrum diagnostic for 1,2-dibromo ethane: molecular mass ion at mass 186, 188 and 190 (1:2:1 in intensity) indicating two bromine atoms on the molecule; major fragment mass ions at 107 and 109 (1:1 in intensity; loss of Br from molecular ion), and at mass 93 and 95 (1:1 in intensity; the $CH_2=Br^+$ ion). This product had an identical GC retention time and mass spectrum with that of an authentic sample of 1,2-dibromo ethane (purchased from Aldrich Chemical Company).

The other product had a GC retention time of 5 minutes and showed the mass spectrum diagnostic for 2-bromoethanol: molecular mass ion at mass 124 and 126 (1:1 in intensity) indicating one bromine atom on the molecule: major fragment mass ions at mass 123 and 125 (1:1 in intensity; loss of H from molecular ion), and at mass 93 and 95 (1:1 in intensity; the $CH_2=Br^+$ ion).

The following summarizes the products obtained as a function of halide concentration in the reaction mixture:

| Product | % of Total Yield | | mM KBr |
|---|---|---|---|
| | 40 | 4200 | |
| Br Br<br>\|  \|<br>$CH_2-CH_2$ | 1 | 65 | |
| OH Br<br>\|  \|<br>$CH_2-CH_2$ | 99 | 35 | |
| Total Yield | 12.7 mg | 8.2 mg | |

EXAMPLE 12

The procedure for Example 11 was followed, except sodium chloride (23 mg and 2204 mg, respectively; 40 and 3800 mM final) was substituted for potassium bromide.

Two products were detected. The GC column temperature was set at 170° C., isothermal.

One product had a GC retention time of 2 minutes and showed the mass spectrum diagnostic for 1,2-dichloro ethane: molecular mass ion at mass 98, 100 and 102 (10:6:1 in intensity) indicating two chlorine atoms on the molecule, major fragment mass ions at mass 62 and 64 (3:1 in intensity; loss of HCl from molecular ion), and at mass 49 and 51 (3:1 in intensity; the $CH_2=Cl^+$ ion). This product had an indentical GC retention time and mass spectrum with that of an authentic sample of 1,2-dichloro ethane (purchased from Aldrich Chemical Company).

The other product had a GC retention time of 3 minutes and showed the mass spectrum diagnostic for 2-chloro ethanol: molecular mass ion at mass 80 and 82 (3:1 in intensity) indicating one chlorine atom on the molecule; major fragment mass ions at mass 49 and 51 (3:1 in intensity; the $CH_2=Cl^+$ ion), and at mass 44 (loss of HCl from molecular ion).

The following summarizes the products obtained as a function of halide concentration in the reaction mixture:

| Product | % of Total Yield | | mM NaCl |
|---|---|---|---|
| | 40 | 3800 | |
| Cl Cl<br>\|  \|<br>$CH_2-CH_2$ | 1 | 43 | |
| OH Cl<br>\|  \|<br>$CH_2-CH_2$ | 99 | 57 | |
| Total Yield | 6.5 mg | 4.2 mg | |

EXAMPLE 13

The procedure of Example 11 was followed, except propylene ($CH_3CH=CH_2$; purchased from Matheson Gas Products) was substituted for ethylene, and lithium bromide (34 mg and 3610 mg, respectively; 40 mM and 4200 mM final) was substituted for potassium bromide.

Three products were detected. The GC column temperature was set at 170° C., isothermal.

One product had a GC retention time of 10 minutes and showed the mass spectrum diagnostic for 1,2-dibromopropane: molecular mass ion at mass 200, 202 and 204 (1:2:1 in intensity) indicating two bromine atoms on the molecule; major fragment mass ions at 121 and 123 (1:1 in intensity; loss of Br from molecular ion), and at mass 93 and 95 (1:1 in intensity; the $CH_2=Br^+$ ion). This product had an identical GC retention time and mass spectrum with that of an authentic sample 1,2-dibromopropane (purchased from Aldrich Chemical Company).

The other two products had GC retention times of 7.8 and 8.2 minutes respectively, and showed the mass spectra diagnostic for propylene bromohydrins. The product having a 7.8 minute retention was the predominant bromohydrin and was identified as 1-bromo-2-propanol: molecular mass ion at mass 138 and 140 (1:1 in intensity) indicating one bromine atom on the molecule; major fragment mass ions at mass 123 and 125 (1:1 in intensity; loss of $CH_3$ from molecular ion), and at mass 45 (the $CH_3CH=OH^+$ ion). The product having a 8.2 minute retention time was identified as 2-bromo-1-propanol.

The following summarizes the products obtained as a function of halide concentration in the reaction mixture:

| Product | % of Total Yield | | mM LiBr |
|---|---|---|---|
| | 40 | 4200 | |
| Br Br<br>\|  \|<br>$CH_3CH-CH_2$ | 1 | 69 | |
| OH Br<br>\|  \|<br>$CH_3CH-CH_2$ | 99 | 31 | |
| Total Yield | 14.2 mg | 10.8 mg | |

EXAMPLE 14

The procedure of Example 5 was followed, except propargyl alcohol (6.7 mg; 12 mM final; $HOCH_2C\equiv CH$; purchased from Aldrich Chemical Company) was substituted for the hydroxy-containing alkenes.

One product was detected. The GC column temperature was set at 190° C., isothermal.

The product had a GC retention time of 15 minutes and showed the mass spectrum diagnostic for 1,2-dibromo-1-propen-3-ol: molecular mass ion at 214, 216 and 218 (1:2:1 in intensity) indicating 2 bromine atoms on the molecule; major fragment mass ion at 135 and 137 (1:1 in intensity; loss of Br from molecular ion).

The following summarizes the products obtained:

| Product | % of Total Yield |
|---|---|
| OH Br Br<br>  \|   \|   \|<br>CH$_2$—C=CH | 100% |
| Total Yield = | 7.5 mg |

EXAMPLE 15

The procedure of Example 14 was followed, except 3-butyn-1-ol (8.4 mg; 12 mM final; HOCH$_2$CH$_2$C≡CH; purchased from Aldrich Chemical Company) was substituted for propargyl alcohol.

One product was detected. The GC column temperature was set at 200° C., isothermal.

The product had a GC retention time of 14 minutes and showed the mass spectrum diagnostic for 1,2-dibromo-1-buten-4-ol: molecular mass ion at mass 228, 230 and 232 (1:2:1 in intensity) indicating 2 bromine atoms on the molecule; major fragment mass ions at mass 198, 200 and 202 (1:2:1 in intensity; loss of CH$_2$O from molecular ion), and at mass 149 and 151 (1:1 in intensity; loss of Br from molecular ion).

The following summarizes the products obtained:

| Product | % of Total Yield |
|---|---|
| OH   Br Br<br>  \|     \|   \|<br>CH$_2$CH$_2$C=CH | 100% |
| Total Yield = | 9.1 mg |

EXAMPLE 16

The procedure of Example 14 was followed, except 2-butyne-1,4-diol (10.3 mg; 12 mM final; HOCH$_2$C≡CCH$_2$OH; purchased from Aldrich Chemical Company) was substituted for propargyl alcohol.

Two products were detected. The GC column temperature was set at 210° C., isothermal.

The major product had a GC retention time of 17 minutes and showed the mass spectrum diagnostic for 2,3-dibromo-2-butene-1,4-diol: molecular mass ion at mass 244, 246, 248 (1:2:1 in intensity) indicating 2 bromine atoms on the molecule; major fragment mass ions at mass 226, 228, 230 (1:2:1 in intensity; loss of H$_2$O from molecular ion), at mass 165 and 167 (1:1 in intensity; loss of Br from molecular ion), and at mass 147 and 149 (1:1 in intensity; loss of Br+H$_2$O from molecular ion).

The minor product was identified as 4-hydroxy-2-butyn-1-al (HOCH$_2$C≡CCHO).

The following summarizes the products obtained:

| Product | % of Total Yield |
|---|---|
| OH Br Br OH<br>  \|   \|   \|   \|<br>CH$_2$—C=C—CH$_2$ | 98 |
| OH<br>  \|<br>CH$_2$C≡C—CHO | 2 |
| Total Yield = | 8.9 mg |

EXAMPLE 17

The procedure of Example 6 was followed, except 1-phenyl-1-propyne (14.1 mg; 12 mM final; C$_6$H$_5$C≡CCH$_3$; purchased from Aldrich Chemical Company) was substituted for 2-butene-1,4-diol.

Two products were detected. The GC column temperature was set at 220° C., isothermal.

One product had a GC retention time of 9 minutes and showed the mass spectrum diagnostic for 1,2-dichloro-1-phenyl-1-propene: molecular mass ion at mass 186, 188 and 190 (10:6:1 in intensity) indicating two chlorine atoms on the molecule; major fragment mass ion at mass 115 (loss of HCl$_2$ from molecular ion).

The other product had a GC retention time of 12 minutes and showed the mass spectrum diagnostic for 1,1-dichloroethyl phenyl ketone: molecular mass ion not detected; major fragment mass ions at mass 166 and 168 (3:1 in intensity; loss of HCl from molecular ion), at mass 105 (the C$_6$H$_5$C≡O$^+$ ion), and at mass 77 (the C$_6$H$_5$$^+$ ion).

The following summarizes the products obtained as a function of halide concentration in the reaction mixture:

| Product | % of Total Yield |
|---|---|
| Cl Cl<br>  \|   \|<br>C$_6$H$_5$C=CCH$_3$ | 43 |
| O<br>  \|\|<br>C$_6$H$_5$CC(Cl)$_2$CH$_3$ | 57 |
| Total Yield = | 8.7 mg |

EXAMPLE 18

The procedure of Example 11 was followed, except methyl acetylene (CH$_3$C≡CH; purchased from Matheson Gas Products) was substituted for ethylene.

Four products were detected. The GC column temperature was set at 170° C., isothermal.

One product had a GC retention time of 9 minutes and showed the mass spectrum diagnostic for 1,2-dibromo-1-propene: molecular mass ion at mass 198, 200 and 202 (1:2:1 in intensity) indicating two bromine atoms on the molecule; major fragment mass ion at mass 119 and 121 (1:1 in intensity; loss of Br from molecular ion).

Another product had a GC retention time of 7 minutes and showed the mass spectrum diagnostic for bromo acetone: molecular mass ion at 136 and 138 (1:1 in intensity) indicating 1 bromine atom on the molecule; major fragment mass ions at mass 93 and 95 (1:1 in intensity; the CH$_2$=Br$^+$ ion) and at mass 57 (loss of Br from molecular ion).

Two other products had GC retention time of 13 and 17 minutes and showed the mass spectra diagnostic for dibromo acetones. The product having a 13 minute retention time was identified as 1,1-dibromo acetone: molecular mass ion at mass 214, 216 and 218 (1:2:1 in intensity) indicating two bromine atoms on the molecule; major fragment mass ions at mass 171, 173 and 175 (1:2:1 in intensity; loss of CH$_3$CO from molecular ion), and at mass 43 (the CH$_3$C≡O$^+$ ion). The product having a 17 minute retention time was identified as 1,3-dibromo acetone: molecular mass ion at mass 214, 216 and 218 (1:2:1 in intensity) indicating two bromine atoms on the molecule; major fragment mass ions at mass 121 and 123 (1:1 in intensity; loss of CH$_2$Br from molecular ion), and at mass 93 and 95 (1:1 in intensity; the CH$_2$=Br$^+$ ion).

The following summarizes the products obtained as a function of halide concentration in the reaction mixture:

| Product | % of Total Yield | | mM KBr |
|---|---|---|---|
| | 40 | 4200 | |
| Br Br<br> \|  \|<br>CH$_3$C=CH | 1 | 58 | |
| O<br>\|\|<br>CH$_3$CCH$_2$Br | 30 | 1 | |
| O<br>\|\|<br>CH$_3$CCHBr$_2$ | 42 | 40 | |
| O<br>\|\|<br>BrCH$_2$CCH$_2$Br | 27 | 1 | |
| Total Yield | 13.1 mg | 8.9 mg | |

EXAMPLE 19

The procedure of Example 2 was followed, except 2-cyclohexen-1-ol (11.8 mg; 12 mM final; C$_6$H$_{10}$O; purchased from Aldrich Chemical Company) was substituted for allyl alcohol. The final concentrations of potassium bromide in the reactions were 40 mM and 4200 mM, respectively.

Three products were detected. The GC column temperature was set at 200° C., isothermal.

One product had a GC retention time of 8 minutes and showed the mass spectrum diagnostic for 1,2-dibromo-3-cyclohexanol: molecular mass ion at mass 256, 258 and 260 (1:2:1 in intensity) indicating two bromine atoms on the molecule; major fragment mass ions at mass 177 and 179 (1:1 in intensity; loss of Br from molecular ion), at mass 159 and 161 (1:1 in intensity; loss of Br+H$_2$O from molecular ion), and at mass 97 (loss of HBr$_2$ from molecular ion).

The other two products had a GC retention time of 5 minutes and showed the mass spectrum diagnostic for 1-bromo-2,3-cyclohexanediol and 2-bromo-1,3-cyclohexanediol: molecular mass ion not detected; major fragment mass ion at mass 193 and 195 (1:1 in intensity; loss of H from molecular ion), at mass 177 and 179 (1:1 in intensity; loss of OH from molecular ion), at mass 114 (loss of HBr from molecular ion), and at mass 97 (loss of Br+H$_2$O from molecular ion).

The following summarizes the products obtained as a function of halide concentration in the reaction mixture.

| Product | % of Total Yield | | mM KBr |
|---|---|---|---|
| | 40 | 4200 | |
|  | 2 | 75 | |
| 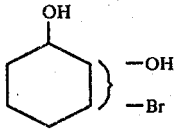 | 98 | 25 | |
| Total Yield | 11.8 mg | 15.3 mg | |

EXAMPLE 20

The procedure of Example 11 was followed, except (1) lactoperoxidase (0.5 ml; Sigma Chemical Company) was substituted for chloroperoxidase and (2) 1,3-butadiene (CH$_2$=CHCH=CH$_2$; purchased from Matheson Gas) was substituted for ethylene. The reactions were run in pH 6.5 potassium phosphate buffer.

Five products were detected. The GC column temperature was set at 170° C. initially, and then programmed up to 250° C. at a rate of 10° C./minute.

One product had a GC retention time of 6 minutes and showed the mass spectrum diagnostic for 1,2-dibromo-3-butene: molecular mass ion not detected; major fragment mass ions at mass 133 and 135 (1:1 in intensity; loss of Br from molecular ion), at mass 93 and 95 (1:1 in intensity; the CH$_2$=Br$^+$ ion), and at mass 79 and 81 (1:1 in intensity; the Br$^+$ ion).

A second product had a GC retention time of 3 minutes and showed the mass spectrum diagnostic for 1-bromo-3-buten-2-ol: molecular mass ion not detected; major fragment mass ions at mass 149 and 151 (1:1 in intensity; loss of H from molecular ion), at mass 123 and 125 (1:1 in intensity; loss of C$_2$H$_3$ from molecular ion) at mass 71 (loss of Br from molecular ion), and at mass 57 (loss of CH$_2$Br from molecular ion).

Another product had a GC retention time of 10 minutes and showed the mass spectrum diagnostic for 1,2,4-tribromo-3-butanol: molecular mass ion not detected; major fragment mass ions at mass 229, 231 and 233 (1:2:1 in intensity; loss of Br from molecular ion), at mass 215, 217 and 219 (1:2:1 in intensity; loss of Br+CH$_2$OH from molecular ion), and at mass 123 and 125 (1:1 in intensity; loss of C$_2$H$_3$Br$_2$ from molecular ion).

Two other products had GC retention times of 7 and 8 minutes respectively, and showed the mass spectra diagnostic for dibromobutanediols. The product having a 7 minute retention time was the predominant isomer and was identified as 1,4-dibromo-2,3-butanediol: molecular mass ion not detected; major fragment mass ions at mass 166 and 168 (1:1 in intensity; loss of HBr from molecular ion), at mass 153 and 155 (1:1 in intensity; loss of CH$_2$Br from molecular ion), and at mass 123 and 125 (1:1 in intensity; the BrCH$_2$CH=OH$^+$ ion).

The product having an 8 minute retention time was identified at 1,3-dibromo-2,4-butanediol.

The following summarizes the products obtained as a function of halide concentration in the reaction mixture:

| Product | % of Total Yield | | |
|---|---|---|---|
| | 40 | 4200 | mM KBr |
| $CH_2=CHCH(Br)-CH_2(Br)$ | 1 | 71 | |
| $CH_2=CHCH(OH)-CH_2(Br)$ | 79 | 5 | |
| $CH_2(Br)-CH(Br)CH(OH)-CH_2(Br)$ | 2 | 23 | |
| $CH_2(Br)-CH(OH)CH(OH)-CH_2(Br)$ | 18 | 1 | |
| Total Yield | 17.6 mg | 16.9 mg | |

U.S. Pat. No. 3,528,886 September 1970 Neidleman et al.
U.S. Pat. No. 3,934,037 January 1976 Lewis et al.
U.S. Pat. No. 4,113,746 September 1978 Kawabe et al.
U.S. Pat. No. 4,125,733 November 1978 Sandler
U.S. Pat. No. 4,274,641 January 1981 Neidleman et al.
U.S. patent application No. 229,554, filed Jan. 29, 1981 by Neidleman et al.
Cooney, C. L. and Hueter, J., *Biotech. and Bioeng.*, 16:1045–1053 (1974).
Kollonitsch, S., Marburg, S., and Perkins, L. M., *J. Am. Chem. Soc.*, 92:4489–4490 (1970).
Lowenheim, F. A. and Moran, M. K., *Faith, Keyes, and Clark's Industrial Chemicals*, 4th Ed. New York, Wiley, 1975 pp. 389–391.
Morris, D. R. and Hager, L. P., *J. Biol. Chem.*, 241:1763–1768 (1966).
Weissermel, K. and Arpe, H. J., *Industrial Organic Chemistry: important raw materials and intermediates*, New York, Verlag Chemie, 1978, pp. 191–200.

What is claimed is:

1. A method of converting an alkene or alkyne selected from the group consisting of allyl alcohol, 3-buten-1-ol, 3-buten-2-ol, 2-butene-1,4-diol, allyl chloride, allyl bromide, ethylene, propylene, propargyl alcohol 3-butyn-1-ol, 2-butyne-1,4-diol, methyl acetylene, 2-cyclohexen-1-ol and 1,3-butadiene to produce the corresponding vicinal dihalogenated product in an amount of at least 65% of the total product formed, said method comprising reacting said compound in an aqueous medium with a haloperoxidase enzyme in the presence of $H_2O_2$ and an alkali metal halide selected from the group consisting of alkali metal chloride, bromide, and iodide, at a halide ion concentration of at least 1 M.

2. The method of claim 1, wherein the haloperoxidase includes chloroperoxidase.

3. The method of claim 1, wherein the haloperoxidase includes lactoperoxidase and the halide ion is selected from the group consisting of bromide and iodide.

4. The method of claim 1, wherein the haloperoxidase includes horseradish peroxidase, and the halide ion includes iodide.

5. The method of claim 1, wherein the $H_2O_2$ is generated in situ enzymatically.

6. The method of claim 5, wherein $H_2O_2$ is generated enzymatically by the reaction of a glucose oxidase with D-glucose.

7. The method of claim 1, wherein the compound includes allyl alcohol, the halide includes chloride at a concentration above about 2 M, and the dichlorinated product comprises at least about 90% of the total product formed.

8. The method of claim 7, wherein the haloperoxidase includes *C. fumago* chloroperoxidase.

9. The method of claim 1, wherein the compound includes allyl alcohol, the halide includes bromide at a concentration up to about 4 M, and the dibrominated product comprises at least about 98% of the total product formed.

10. The method of claim 9, wherein the haloperoxidase includes lactoperoxidase.

11. The method of claim 1, wherein the compound includes allyl alcohol, the halide includes iodide, and the diiodinated product comprises at least about 70% of the total product formed.

12. The method of claim 11, wherein the haloperoxidase includes horseradish peroxidase.

13. The method of claim 1 wherein the compound is selected from one of the group consisting of 3-buten-1-ol and 3-buten-2-ol, the halide includes bromide at a concentration of at least about 3 M, and the dibrominated product comprises at least about 80% of the total product formed.

14. The method of claim 13, wherein the haloperoxidase includes *C. fumago* chloroperoxidase.

15. The method of claim 1, wherein the compound includes 2-butyne-1,4-diol, the halide includes chloride at a concentration of at least about 2 M, and the dichlorinated product comprises substantially 100% of the total product formed.

16. The method of claim 15, wherein the haloperoxidase includes *C. fumago* chloroperoxidase.

17. The method of claim 1, wherein the compound includes 2-butyne-1,4-diol, the halide includes bromide at a concentration of at least about 3 M, and the dibrominated product comprises at least about 90% of the total product formed.

18. The method of claim 17, wherein the enzyme includes *C. fumago* chloroperoxidase.

19. The method of claim 1, wherein the compound includes allyl chloride, the halide includes bromide at the concentration of at least about 4 M, and the dibrominated product comprises at least about 80% of the total product formed.

20. The method of claim 19, wherein the enzyme includes *C. fumago* chloroperoxidase.

21. The method of claim 1, wherein the compound includes allyl bromide, the halide includes bromide at a concentration of about 4 M, and the tribrominated product comprises at least about 75% of the total product formed.

22. The method of claim 21, wherein the haloperoxidase is *C. fumago* chloroperoxidase.

23. The method of claim 1, wherein the compound includes ethylene, the halide includes bromide at a concentration of at least about 4 M, and the dibrominated product comprises at least about 65% of the total product formed.

24. The method of claim 23, wherein the haloperoxidase includes *C. fumago* chloroperoxidase.

25. The method of claim 1, wherein the compound includes propylene, the halide includes bromide, at a concentration of at least about 4 M, and the dibrominated product comprises at least about 65% of the total product formed.

26. The method of claim 25, wherein the haloperoxidase includes *C. fumago* chloroperoxidase.

27. The method of claim 1, wherein the compound includes propargyl alcohol, the halide includes bromide, at a concentration of at least about 3 M, and the dibrominated product comprises substantially 100% of the total product formed.

28. The method of claim 27, wherein the enzyme includes *C. fumago* chloroperoxidase.

29. The method of claim 1, wherein the compound includes 3-butyn-1-ol, the halide includes bromide at a concentration thereof of at least about 3 M, and the dibrominated product comprises substantially 100% of the total product formed.

30. The method of claim 29, wherein the haloperoxidase includes *C. fumago* chloroperoxidase.

31. The method of claim 1, wherein the compound includes 2-butyne-1,4-diol, the halide includes bromide at a concentration of at least about 3 M, and the dibrominated product comprises at least about 95% of the total product formed.

32. The method of claim 31, wherein the haloperoxidase includes *C. fumago* chloroperoxidase.

33. The method of claim 1, wherein the compound includes methyl acetylene, and the halide includes bromide at a concentration of at least about 4 M.

34. The method of claim 33, wherein the haloperoxidase includes *C. fumago* chloroperoxidase.

35. The method of claim 1, wherein the compound includes 2-cyclohexen-1-ol, the halide includes bromide at a concentration of of at least about 3 M, and the dibrominated product comprises at least about 70% of the total product formed.

36. The method of claim 35, wherein the haloperoxidase includes lactoperoxidase.

37. The method of claim 1, wherein the compound includes 1,3-butadiene, the halide includes bromide at a concentration of at least about 4 M, and the dibrominated product comprises at least about 70% of the total product formed.

38. The method of claim 37, wherein the haloperoxidase includes lactoperoxidase.

* * * * *